United States Patent [19]

Moss et al.

[11] Patent Number: 5,869,453
[45] Date of Patent: Feb. 9, 1999

[54] CYTOTOXIC T-CELL EPITOPES

[75] Inventors: Denis James Moss, Arana Hills; Scott Renton Burrows, Bald Hills; Rajiv Khanna, Hentson; Beverley Mavis Kerr, Gumdale; Jacqueline Margaret Burrows, Bald Hills; Andreas Suhrbier, Newmarket, all of Australia

[73] Assignee: The Council of the Queensland Institute of Medical Research, Queensland, Australia

[21] Appl. No.: 704,655

[22] PCT Filed: Mar. 16, 1995

[86] PCT No.: PCT/AU95/00140

§ 371 Date: Jan. 27, 1997

§ 102(e) Date: Jan. 27, 1997

[87] PCT Pub. No.: WO95/24925

PCT Pub. Date: Sep. 21, 1995

[30] Foreign Application Priority Data

Mar. 16, 1994 [AU] Australia ............................. PM 4465

[51] Int. Cl.[6] .............................. A61K 38/00; C07K 5/00
[52] U.S. Cl. .............................. 514/16; 514/13; 514/613; 530/328; 530/326; 530/327
[58] Field of Search ................................. 514/16, 13, 613; 530/326, 328, 327

[56] References Cited

FOREIGN PATENT DOCUMENTS

WO 93/19092  9/1993  WIPO .
WO 94/18234  8/1994  WIPO .
WO 95/30015  11/1995  WIPO .

OTHER PUBLICATIONS

Burrows et al., "Rapid visual assay of cytotoxic T–cell specificity utilizing synthetic peptide induced T–cell — T–cell killing", Immunology, 76:174–175, 1992.

Araget, et al., "Dominant Selection of an Invariant T Cell Antigen Receptor in Response to Persistent Infection by Epstein–Barr Virus", J. Exp. Med., 108:2335–2340, 1994.

Baer, et al., DNA sequence and expression of the B95–8 Epstein–Barr virus genome, Nature 310:207–211, 1984.

Brooks, et al., "Different HLA–B27 subtypes present the same immunodominant Epstein–Barr virus peptide" J. Exp. Med., 178/3 (879–887) 1993.

Burrows, et al., "An Epstein–Barr Virus–Specific Cytotoxic T–Cell Epitope Present on A– and B–Type Transformants", Journal of Virology 64:3974–3976, 1996.

Burrows, et al., "Identification of a Naturally Occurring Recombinant Epstein–Barr Virus Isolate from New Guinea That Encodes both Type 1 and Type 2 Nuclear Antigen Sequences", Journal of Virology 7:4829–4833, 1996.

Burrows, et al., "Unusually high frequency of Epstein–Barr virus genetic variants in Papua New Guinea that can escape cytotoxic T–cell recognition: Implications for virus evolution" Journal of Virology 70:2490–2496. 1996.

Burrows, et al., "Five new cytotoxic T cell epitopes identified within Epstein–Barr virus nuclear antigen 3." J Gen Virol 75:2489–93, 1994.

Burrows, et al., An alloresponse in humans is dominated by cytotoxic T lymphocytes (CTL) cross–reactive with a single Epstein–Barr virus CTL epitope: implications for graft–versus–host disease. J. Exp. Med, 179:1155–61, 1994.

Burrows, et al., "The specificity of recognition of a cytotoxic T lymphocyte epitope", Eur. J. Immunol 22:191–195, 1992.

Burrows, et al., "An Epstein–Barr Virus–Specific Cytotoxic T Cell Epitope in EBV Nuclear Antigen 3 (EBNA 3)", J. Exp. Med. 171:345–349, 1990.

Burrows, et al., "Patterns of Reactivity of Epstein–Barr Virus Specific T Cells in A–Type Donor Cultures after Reactivation with Autologous A– or B– Type Transformants", Cellular Immunology 127:47–55, 1990.

Buseyne, et al., "Gag–specific cytotoxic T lymphocytes from human immunodeficiency virus type 1–infected individuals: Gag epitopes are clustered in three regions of the p24(gag) protein" J. Virol USA, 67:694–702, 1993.

de Campos–Lima, et al., "T cell responses and virus evolution: loss of HLA A11–restricted CTL epitopes in Epstein–Barr virus isolates from highly A11–positive populations by selective mutation of anchor residues", J. Exp. Med. 179:1297–305, 1994.

Khanna, et al., "Isolation of cytotoxic T lymphocytes from healthy seropositive individuals specific for peptide epitopes from Epstein–Barr virus nuclear antigen 1: implications for viral persistence and tumor surveillance", Virology 214:633–637, 1995.

Khanna, et al., "Immune regulation in Epstein–Barr virus–associated diseases", Microbiol Rev 59:387–405, 1995.

Khanna, et al., "EBV peptide epitope sensitization restores human cytotoxic T cell recognition of Burkitt's lymphoma cells. Evidence for a critical role for ICAM–2." J. Immunol, 150:5154–62, 1993.

Khanna, et al., "Presentation of endogenous viral peptide epitopes by anti–CD40 stimulated human B cells following recombinant vaccinia infection", J. Immunol Methods 164:41–49, 1993.

Khanna, et al., "Localization of Epstein–Barr virus cytotoxic T cell epitopes using recombinant vaccinia: Implications for vaccine development", J. Exp. Med., 176:169–176, 1992.

(List continued on next page.)

Primary Examiner—Lila Feisee
Assistant Examiner—Geetha P. Bansal
Attorney, Agent, or Firm—Arnold, White & Durkee

[57] ABSTRACT

The present invention provides cytotoxic Epstein-Barr virus T-cell epitopes. The epitopes are selected from the group consisting of QAKWRLQTL, RYSIFFDY, HLAAQGMAY, YPLHEQHGM, SVRDRLARL, AVLLHEESM, VSFIEFVGW, FRKAQIQGL, PYLFWLAAI, TVFYNIPPMPL, PGDQLPGFSDGRACPV, VEITPYKPTW, and variants thereof. In addition, the present invention provides compositions including these epitopes for use in inducing CTL's in a subject.

16 Claims, 3 Drawing Sheets

OTHER PUBLICATIONS

Khanna, et al., "Expression of Epstein–Barr virus nuclear antigens in anti–IgM–stimulated B cells following recombinant vaccinia infection and their recognition by human cytotoxic T cells", *Immunology*, 74:504–10, 1991.

Kyaw–Tanner, et al., "Epstein–Barr Virus–Specific Cytotoxic T Cell Response in Cardiac Transplant Recipients", *Transplantation* 57:1611–1617, 1994.

Lee, et al., "Epstein–Barr virus isolates with the major HLA B35.01–restricted cytotoxic T lymphocyte epitope are prevalent in a highly B35.01–positive African population", *Eur. J. Immunol* 25:102–110, 1995.

Lee, et al., "HLA A2.1–restricted cytotoxic T cells recognizing a range of Epstein–Barr virus isolates through a defined epitope in latent membrane protein LMP2", *J. Virol.* 67:7428–7435, 1993.

Lees, et al., "The Epstein–Barr virus candidate vaccine antigen gp340/220 is highly conserved between virus types A and B.", *Virology* 195:578–586, 1993.

Levitsky, et al., "The life span of major histocompatibility complex–peptide complexes influences the efficiency of presentation and immunogenicity of two class I–restricted cytotoxic T lymphocyte epitopes in the Epstien–Barr virus nuclear antigen 4", *J. Exp. Med.* 183:915–926, 1996.

Misko, et al., "Failure of Epstein–Barr virus–specific cytotoxic T lymphocytes to lyse B cells transformed with the B95–8 strain is mapped to an epitope that associates with the HLA–B8 antigen", *Clin. exp. Immunol*, 87:65–70, 1992.

Misko, et al., "Cytotoxic T lymphocyte discrimination between type A Epstein–Barr virus transformants is mapped to an immunodominant epitope in EBNA 3", *J. Gen. Virol.* 72:405–409, 1991.

Misko, et al., "T lymphocytes in infectious mononucleosis; Effect on IL–2 on the outgrowth of Epstein–Barr virus–infected cells", *Immunol. Cell Biol.* 67:49–55, 1989.

Morioka, et al., "A decapeptide (Gln–Asp–Leu–Thr–Met–Lys–Tyr–Gln–Ile–Phe) from human melanoma is recognized by CTL in melanoma patients", *J. Immunol.*153:5650–5658, 1994.

Moss, et al., "Potential antigenic targets on Epstein–Barr virus–associated tumours and the host response", *Ciba Found Symp.*, 187:4–13; discussion 13–20, 1994.

Moss, et al., T Cell—T Cell Killing Is Induced by Specific Epitopes: Evidence for an Apoptotic Mechanism, *J. Exp. Med.* 173:681–686, 1991.

Moss, et al., "Cytotoxic T–cell clones discriminate between A– and B–type Epstein–Barr virus transformants", *Nature* 331:719–721, 1988.

Moss, et al., Calcium Concentration Defines Two Stages in Transformation of Lymphocytes By Epstein–Barr Virus, *Int. J. Cancer* 33:587–590, 1984.

Moss, et al., Epstein–Barr Virus Specific T–Cell Response in Nasopharyngeal Carcinoma Patients, *Int. J. Cancer* 32:301–305, 1983.

Moss, et al., A Comparison of Epstein–Barr Virus–Specific T–Cell Immunity in Malaria–Endemic and –Nonendemic Regions of Papua New Guinea, *Int. J. Cancer*, 31:727–732, 1983.

Murray, et al., "Human cytotoxic T–cell responses against Epstein–Barr virus nuclear antigens demonstrated by using recombinant vaccinia viruses", *Proc. Natl. Acad. Sci. USA* 87:2906–2910, 1990.

Pither, et al., "Distribution of epitopes within the amino acid sequence of the Epstein–Barr virus major envelope glycoprotein, gp340, recognized by hyperimmune rabbit sera", *J. Gen Virol,* 73:1409–1415, 1992.

Rowe, et al., "Restoration of endogenous antigen processing in Burkitt's lymphoma cells by Epstein–Barr virus latent membrane protein–1: coordinate up–regulation of peptide transporters and HLA–class I antigen expression", *Eur. J. Immunol.* 25:1374–1384 1995.

Rowe, et al., Distinction between Epstein–Barr virus type A (EBNA 2A) and type B (EBNA 2B) isolates extends to the EBNA 3 family of nuclear proteins, *J. Virol.* 63:1031–1039, 1989.

Schmidt, et al. "Nonresponsiveness to an immunodominant Epstein–Barr virus–encoded cytotoxic T–lymphocyte epitope in nuclear antigen 3A: implications for vaccine strategies", *Proc. Natl. Acad. Sci. U S A* 88:9478–9482, 1991.

Thomson, et al, "Minimal epitopes expressed in a recombinant polyepitope protein are processed and presented to CD8+ cytotoxic T cells: implications for vaccine design", *Proc. Natl. Acad. Sci.* 92:5845–5489, 1995.

Wallace, et al., "Identification of two T–cell epitopes on the candidate Epstein–Barr virus vaccine glycoprotein gp340 recognized by CD4+ T–cell clones", *J. Virol.*65:3821–3828, 1991.

White, et al., "Recruitment during infectious mononucleosis of CD3+CD4+CD8+ virus–specific cytotoxic T cells which recognise Epstein–Barr virus lyticantigen BHRF1", *Virology* 219:489–492, 1996.

Rovinsky et al Modern Vaccinology Ed E Kurstak Plenum Medical, New York 1994 Chapter 9 p. 191 sp pp. 194–197.

CYTOTOXIC T-CELL EPITOPES

FIELD OF THE INVENTION

The present invention relates to cytotoxic T-cell (CTL) epitopes within Epstein-Barr virus. The present invention also relates to the use of the epitopes in subunit vaccines.

BACKGROUND OF THE INVENTION

Epstein-Barr virus (EBV) is a herpes virus that infects approximately 80% of individuals in Western societies. Following primary infection, a life long latent EBV infection of B cells is established. When primary infection is delayed until adolescence, which occurs in 10–20% of individuals in Western societies, there is an approximately 50% chance of developing infectious mononucleosis.

EBV has the very useful property of being able to "immortalise" or transform human B cells. These transformed B cells (referred to as LCLs) have the potential for essentially unlimited growth in the laboratory. There are two methods by which these LCLs can be established. Firstly, they may be established by the use of a common strain of EBV, referred to as B95.8. The LCL that is established is infected with this strain of virus. Secondly, LCLs may be generated using the latently infected B cells, present in all EBV immune individuals as a source of transforming virus. In this case, the LCL that emerges is transformed with the strain of EBV naturally present in any given EBV immune individual (referred to as spontaneous LCL).

There are two EBV types, A and B. The A type appears to predominate in the majority of lymphoid infections of healthy seropositive individuals. In such individuals, latently infected B cells appear to be controlled by CD8+ cytotoxic T cells (CTL) specific for the latent antigens, which include the EBV nuclear antigens (EBNAs) 2–6 and the latent membrane antigens (LMP) 1–3 (Moss, D. J. et al. 1992). Recent developments suggests that CD4+ CTL may also play a part in controlling this infection. These CTL are known to recognise short peptide epitopes derived from antigenic determinants in association with MHC class I molecules on the surface of an appropriate antigen presenting cell. LCLs displaying HLA class I and II alleles and presenting epitopes within EBV latent antigens are frequently used as a target cell for defining the specificity of CTL clones.

As whole virus or recombinant vaccines based on full length latent proteins are considered potentially oncogenic, an EBV vaccine based on CTL epitopes derived from the latent antigens is currently being developed (Moss, D. J. et al 1993). Khanna et al, (1992) have previously described several CTL epitopes.

SUMMARY OF THE INVENTION

In a first aspect the present invention consists in cytotoxic T-cell epitopes from Epstein-Barr virus.

More specifically, there is provided twelve cytotoxic T-cell epitopes from the Epstein-Barr virus latent antigens having the amino acid sequences QAKWRLQTL SEQ ID NO:11, RYSIFFDY SEQ ID NO:13, HLAAQGMAY SEQ ID NO:5, YPLHEQHGM SEQ ID NO:23 (YPLHKOHGM SEQ ID NO:25, YRLHEOHGM SEQ ID NO:26, YPLHEORGM SEQ ID NO:24) SVRDRLARL SEQ ID NO:15, AVLLHEESM SEQ ID NO:1 (TVLLHEESM SEQ ID NO:19 and TALLHEESM SEQ ID NO:16), VSFIEFVGW SEQ ID NO:22, FRKAQIQGL SEQ ID NO:3, PYLFWLAAI SEQ ID NO:10, TVFYNIPPMPL SEQ ID NO:18, PGDQLPGFSDGRACPV SEQ ID NO:9 and VEITPYKPTW SEQ ID NO:20. In addition, the underlined amino acid sequences in brackets are variants of the aforementioned sequence and have been sequenced from geographically different isolates of Epstein-Barr virus. It has not as yet been established whether these variants are CTL epitopes.

In a second aspect the present invention consists in a composition for use in inducing CTL's in a subject, the composition comprising at least one cytotoxic Epstein-Barr virus T-cell epitope according to the first aspect of the present invention in admixture with at least one pharmaceutical acceptable adjuvant, carrier, diluent or excipient.

In a third aspect the present invention consists in a method of preparing a composition for use in inducing CTL's in a subject, the method comprising admixing at least one cytotoxic Epstein-Barr virus T-cell according to the first aspect of the present invention with at least one pharmaceutical acceptable adjuvant, carrier, diluent or excipient.

As used herein the term "subject" is intended to cover human and non-human animals.

BEST METHOD OF CARRYING OUT THE INVENTION

Figure 1:
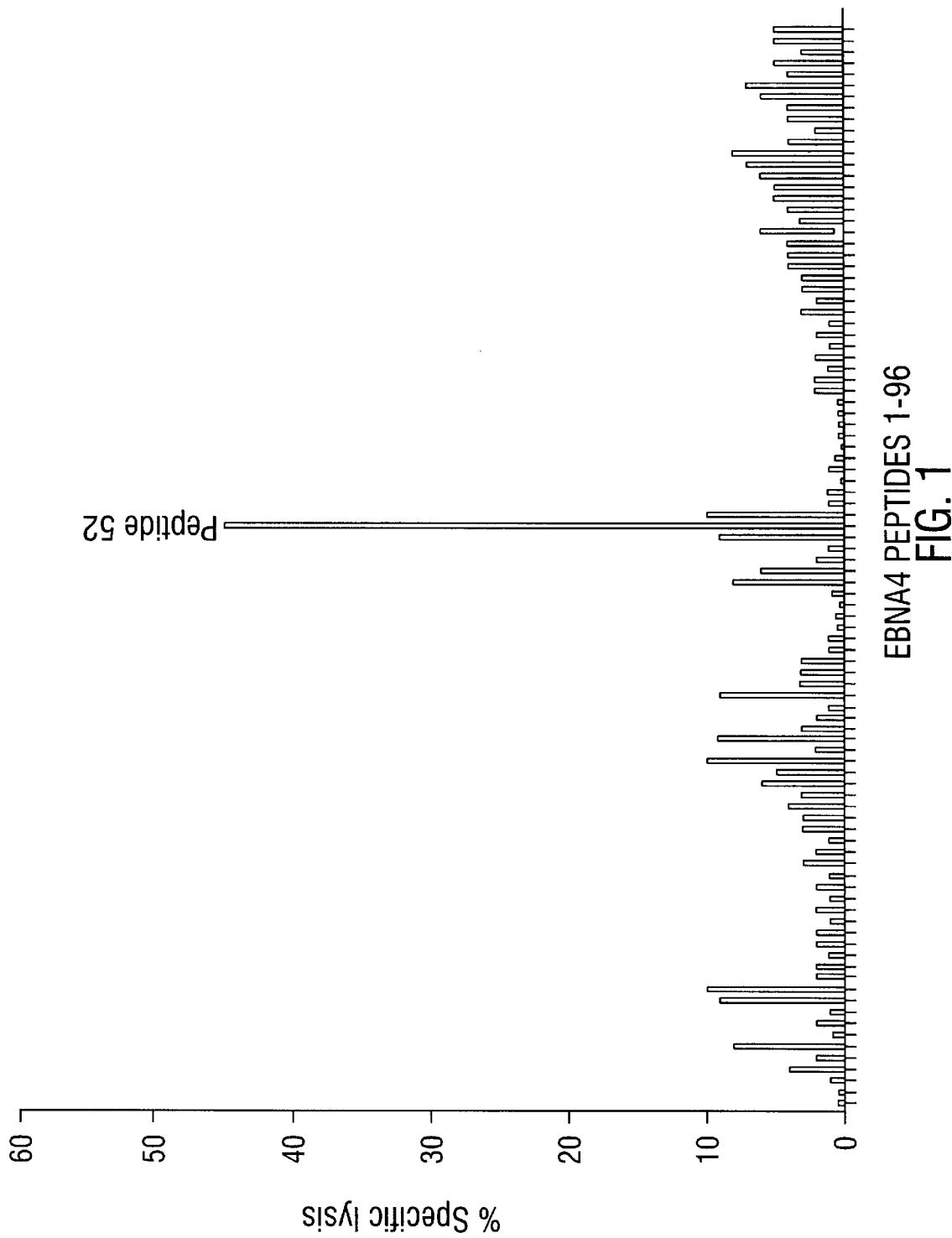
FIG. 1. Screening overlapping peptides of EBNA4 on PHA blast cells for reactivity.

The following examples illustrate the localisation of twelve new CTL epitopes within the EBV latent antigens using an overlapping peptide net spanning the relevant EBV antigen. The peptides were synthesised using the sequence of the B95.8 strain of EBV (Baer et al 1990). In addition, field isolates from different geographic locations were sequenced at the site of CTL epitopes YLPHEQHGM and AVLLHEESM and variants of these epitopes defined.

Abbreviations
CTL cytotoxic T-cell lymphocyte
E effector
EBV Epstein-Barr virus
HLA human leucocyte antigen
IL-2 Interleukin-2
LCL lymphoblastoid cell line
PBMC peripheral blood mononuclear cells
PHA phytohaemagglutinin
rIL-2 recombinant Interleukin-2
T target
TCM T cell medium
U/ml units per milliliter

EXAMPLE 1

Basic Culture Media for the Growth of Cells

The medium was RMPI 1640 (Commonwealth Serum Laboratories, Victoria) supplemented with 10% heat-inactivated foetal calf serum, penicillin (100IU/ml) and streptomycin (100 mg/ml). Where indicated, this medium was supplemented with purified recombinant interleukin-2

(rIL-2) (50 U/ml; Hoffman La-Roche) and 30% (v/v) heat-inactivated (56° C., 30 minutes) supernatant from the MLA 144 T-cell line. This supplemented medium was called T-cell medium (TCM) and was used in the culture of phytohaemagglutinin blast cells (PHA blasts) and for the isolation and growth of cytotoxic T-cells (CTL).

EXAMPLE 2
Preparation of Mononuclear Leucocytes and Generation of CTL

Peripheral blood mononuclear cells (PBMC) were separated (400 g or 1500 rpm, 20 minutes) from heparinized (10 U/ml) blood on Ficoll-Paque (Pharmacia, Uppsala, Sweden). The separated PBMCs were washed once in basic media and subsequently used either to stimulate CTL, PHA blasts or to establish EBV transformed cell lines.

EXAMPLE 3
HLA Typing

HLA typing of donors was performed by serology.

EXAMPLE 4
Establishment of Cell Lines 4.1 Establishment of EBV Transformed LCLs by addition of exogenous virus: EBV transformed LCLs were established from PBMCs as follows. The EBV virus stock (Table 1: specific Type and isolate), stored in liquid nitrogen is selected and rapidly thawed at 37° C. Half a milliliter of virus stock ($10^5$ transformation units) is added directly into the PBMC cell pellet ($1-4 \times 10^6$ cells) and incubated for one hour at 37° C. The cells are then washed twice with media at 1000 rpm for five minutes. The cells were then made up in media with PHA (Sigma PHA-P) at 2 $\mu$g/ml and dispensed into a 24 well plate at $2 \times 10^6$ cells/well. Clumps of cells, representing proliferating LCLs, occur within 1–3 weeks after which the cells were transferred into flasks.

4.2 Establishment of spontaneous LCLs by addition as a means of sampling field isolates of the virus: PBMCs from healthy EBV immune individuals from Australia (Brisbane), from Papua New Guinea (Goroka and Madang) or from Kenya were seeded by doubling dilution from $2 \times 10^6$ to $1.25 \times 10^5$ cells per 0.2 ml microtitre plate well in culture medium containing 0.1 mg/ml cyclosporin A (Sandoz Ltd., Basle, Switzerland). The cyclosporin A was maintained in the culture medium in regular refeedings for up to 8 weeks. Wells in which proliferation became apparent were subcultured and expanded at 37° C. This method was used to generate field isolates of the virus.

4.3 Establishment of PHA Blast Cell Lines: PBMC ($2 \times 10^6$ cells/24 well) were stimulated with PHA-P (2 $\mu$g/ml, final concentration) (Sigma) and after three days, TCM was added. Cultures were expanded into flasks and maintained for up to six weeks with bi-weekly replacement of TCM (without further addition of PHA).

4.4 Generation of anti-$\mu$ B cell blasts: PBMCs were separated on Ficoll-Paque (Pharmacia, Uppsala, Sweden) and depleted of T cells using E-rosetting. The enriched B lymphocytes were cultured in growth medium containing anti-IgM ($\mu$-chain specific) coupled to acrylamide beads (Bio-Rad, California, U.S.A.), recombinant human interleukin-4 (rIL-4; 50 U/ml; Genzyme, U.S.A.) and highly purified recombinant human IL-2 from *E. coli* (rIL-2; 20–40 U/ml) (17,18). After 48–72 hr, B cell blasts were suspended in growth medium supplemented with rIL-2 (20–40 U/ml) (14). The B cells continue to divide 2–3 times/week for 3 weeks in the presence of rIL-2. These cells are referred to as anti-$\mu$ B cell blasts.

EXAMPLE 5
Synthesis of Peptides 5.1 Production: Peptides (purchased from Chiron Mimetopes, Melbourne) were synthesised using the pin technology in duplicate on polyethylene pins and cleaved from the pins. A C-terminal glycine ester link was used in the preparation of peptides with acid C-termini (Valerio, R. M. et al 1991).

5.2 Toxicity and Solubilization: Freeze dried peptides were dissolved first in 20 $\mu$l DMSO and then 0.6 ml distilled water to give a concentration of 2 mM. They were stored at 20° C. prior to use. Peptides were diluted in RPMI 1640 for use. Toxicity testing of all the peptides was performed prior to screening by adding peptide at a final concentration of 100 $\mu$M to $10^{4}$ $^{51}$Cr labelled PHA blasts in 200 $\mu$l, in the absence of any effectors.

EXAMPLE 6
Generation of CTLs 6.1 Generation of polyclonal CTLs Polyclonal CTL effectors were generated by stimulating PBMCs from healthy seropositive donors with autologous A-type EBV transformed lymphoblastoid cell lines (LCLs) on days 0 and 7. No IL-2 was added to these cultures, as its presence favoured the expansion of non-specific T-cells (data not shown).

6.2 Agar Cloning of T-Cells. T-cell clones from individual donors were generated as follows. PBMC's were isolated and suspended in medium at a concentration of $2 \times 10^6$ cells in 24 well plates (Costar, Cambridge, Mass.). LCL's from the same donor were irradiated at 8,000 rad and added to each of these wells at either $10^5$ or $10^4$ cells/well. After three days, cells were dispersed and seeded in 3.5 cm diameter culture dishes in 0.35 agarose (Seaplaque, FMC Corp., Rockland, Me.) containing RPMI 1640, 20% 2× RPMI 1640, 20% FCS, 16% MLA supernatant and 50 U/ml rIL-2. Colonies appear within the agar after five days. These are identified under the inverted microscope (×25 magnification) as clusters or chains or discrete cells. These colonies are harvested under the microscope in a laminar flow cabinet by suction into a Gilson pipette. Harvested colonies are dispersed into T-cell growth medium (RPMI 1640, 20% FCS, 30% MLA supernatant and 20 U/ml rIL-2) and transferred to a 96 well microtitre tray containing irradiated LCL's from the same donor ($10^4$ cells/well). These colonies continue to be expanded and are stored in liquid nitrogen (approximately $5 \times 10^6$ cells/ampoule).

EXAMPLE 7
Vaccinia virus recombinants

Recombinant vaccinia constructs for different EBV latent antigens have been previously described (Khanna et al 1992). All EBV sequences were derived from the B95.8 strain of virus. All constructs had the potential to encode the relevant full length EBV protein.

EXAMPLE 8
Chromium Release Assay 8.1 Screening CTL clones for reactivity against recombinant vaccinia encoding EBV latent antigens:

Anti-$\mu$ B cell blasts were infected with recombinant vaccinia viruses at a multiplicity of infection of 10:1 for 1 hour at 37° C. After 14–16 hours, cells were washed with basic culture medium and incubated with $^{51}$Cr for 90 minutes, washed three times and used as targets in a standard 5 hour $^{51}$Cr release assay as described below.

8.2 Peptide Screen: A standard five to six hour chromium release assay was performed on either polyclonal T-cell effectors or T-cell clones, to assess specificity for the peptide epitope. Briefly, washed $^{51}$Cr (Amersham International, England) labelled (60 minutes, 37° C.) target cells (autologous PHA blasts) were added (10$^4$ cells/well in 40 μl) to 10 μl of peptide (final concentration 100 μM) in a U-well 96 well plate (Nunc, Denmark). After a 30 minute incubation at 37° C., between 10$^4$ and 50×10$^4$ effector T-cell (cloned or bulk CTLs), in triplicate, were then added per well in 150 μl, to obtain a final effector to target ratio [E:T] of 50-1:

1. Two controls were added; (i) media and target (background release) and (ii) targets (total release) for addition of 100 μl 0.5 SDS after the five hour incubation. The plate was then centrifuged at 500 rpm for five minutes and incubated at 37° C. for five hours. Following centrifugation at 1000 rpm for five minutes, 100 μl supernatants were removed for gamma counting. Results are expressed as % chromium release calculated as mean counts of experimental wells—mean counts of control (background) wells/by total available counts determined by SDS solubilisation—mean counts of control (background) wells.

EXAMPLE 9

PCR sequencing of EBC isolated from Australia, Papua New Guinea and Kenya

The polymerase chain reaction (PCR) was used to amplify specific EBV DNA sequences in the CTL epitope regions YPLHEQHGM SEQ ID NO:23 and AVLLHEESM SEQ ID NO:1. The purified DNA used in the PCR was from spontaneous LCLs from health individuals from Australia, Papua New Guinea and Kenya. Each DNA sample was subjected to two different PCR reactions. One using primers flanking the known YPLHEQHGM region;

E3YPL5 (GAC GAG ACA GCT ACC AG SEQ ID NO:32)

E3YPL3 (GAG ATA CAG GGG GCA AG SEQ ID NO:33)

and one using primers flanking the known AVLLHEESM epitope region;

E41VT5 (TTG TTG AGG ATG ACG ACG SEQ ID NO:34)

E41VT3 (CAG TAG GGT TGC CAT AAC SEQ ID NO:35)

Each PCR reaction consisted of 1× PCR buffer (Boehringer), 0.2 mM dNTPs, the purified DNA, the respective primers and 1.5 U of Taq polymerase and then subjected to denaturation at 95° C. for 5 minutes followed by 94° C. for 15 seconds, 55° C. for 30 seconds, 72° C. for 15 seconds (35 cycles) using a Perkin Elmer 9600 PCR machine. The PCR products were then purified for sequencing using QIAquick spin columns from Qiagen and sequenced in both directions using the respective primers from the PCR reactions. A PRISM™ Ready Reaction DyeDeoxy™ Terminator Cycle sequencing kit was used to set up the sequencing reaction. Reaction samples were then run on an ABI Cycle Sequencer.

EXAMPLE 10

Identification of CTL Epitopes Within EBV Latent antigens

By way of example of the epitopes described in Table I, the following methodologies were used in the definition of the CTL epitope AVLLHEESM SEQ ID NO:1. The methods used to identify other epitopes were identical. On day 10–11, polyclonal CTLs were used to screen for reactivity against overlapping peptides from EBNA2, EBNA3, EBNA4 and LMP2A on autologous PHA blasts. As seen in FIG. 1, after screening all of the peptides from EBNA4 with polyclonal CTLs from donor CS, a single peptide, referred to as peptide 52 (VTAVLLHEESMQVQVHGSM SEQ ID NO:28) showed strong reactivity in a $^{51}$Cr-release assay.

Figure 2:
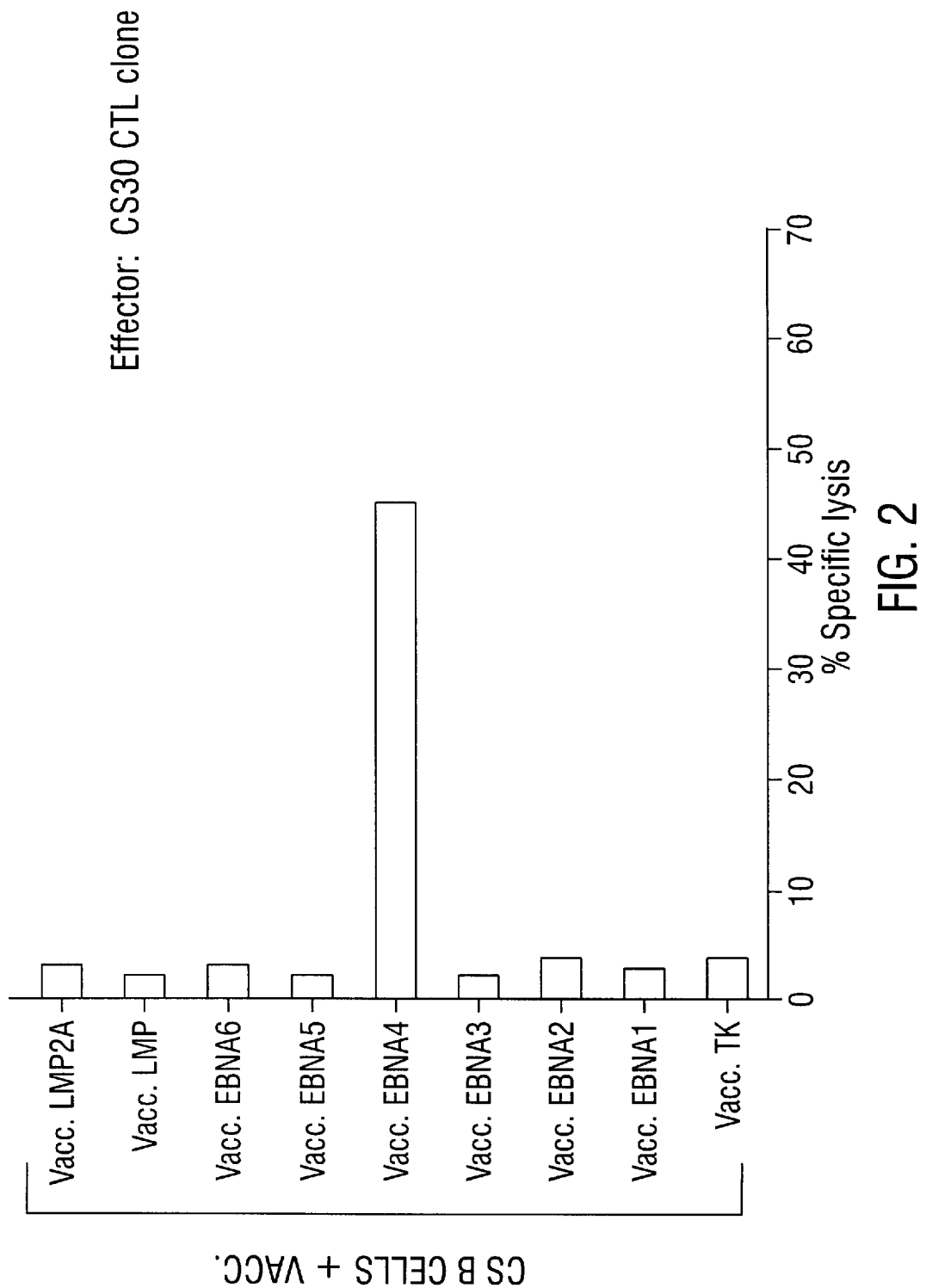
FIG. 2. Reactivity of clone CS30 against a panel of anti-μ B cell blasts infected with recombinant vaccinia virus encoding the EBV latent antigens.

To confirm that this sequence was an active CTL epitope, CTL clones from donor CS were established and screened for reactivity against recombinant vaccinia-infected targets (FIG. 2). As seen in this FIG., clone CS30 recognised B cell blasts infected with recombinant vaccinia encoding EBNA4.

Figure 3:
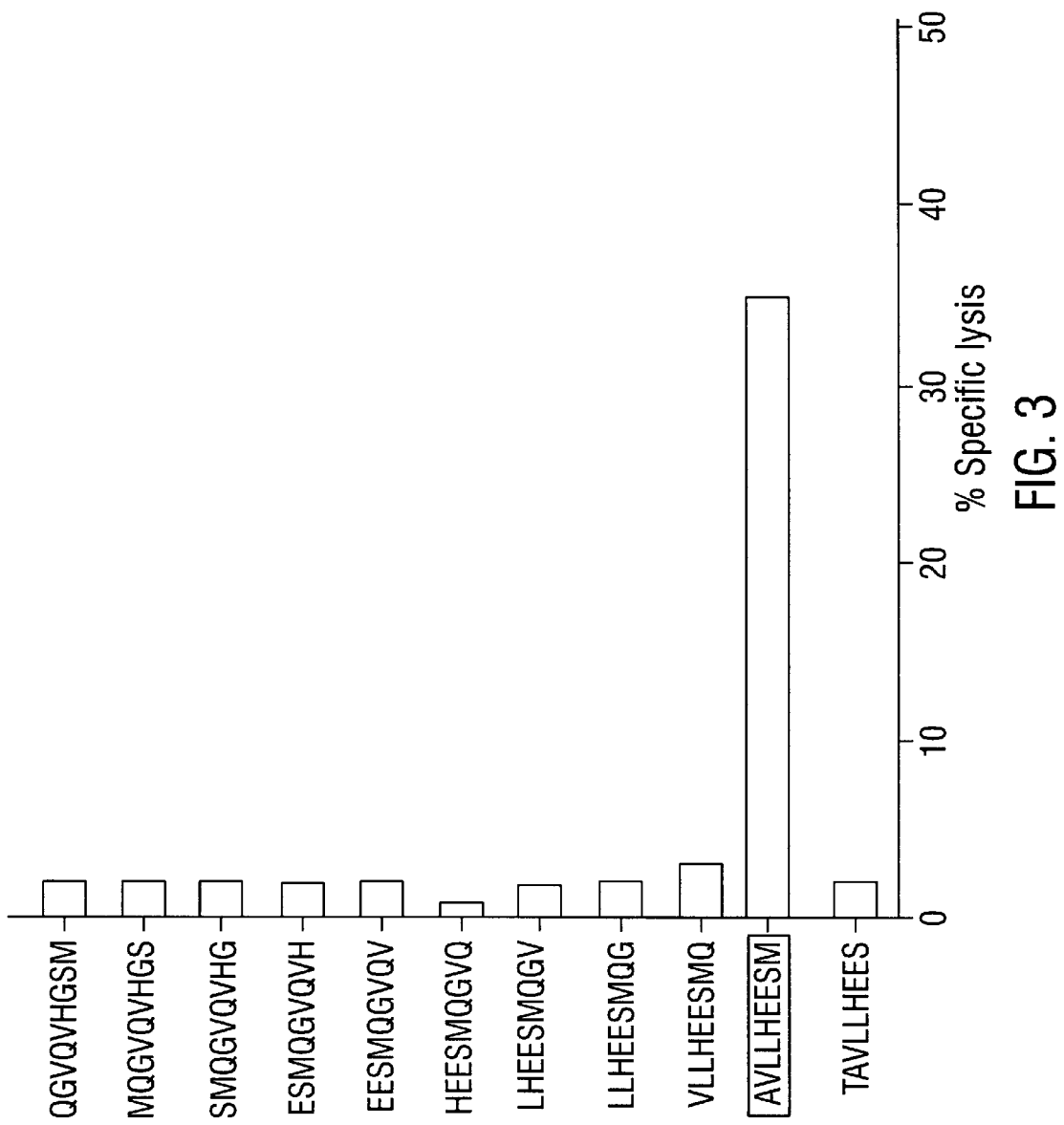
FIG. 3. Minimalisation experiment to define the active epitope sequence within VTAVLLHEESMQGVQVHGSM SEQ ID NO:28. This has enabled the definition of the minimal epitope as AVLLHEESM SEQ ID NO:1.

To minimalise the epitope within this 20 mer sequence, overlapping 9 mer peptides were synthesized, and as can be seen AVLLHEESM SEQ ID NO:1 is the confirmed minimal epitope within the 20 mer peptide. The overlapping peptides from EBNA4 used to demonstrate this minimal overlapping sequence are listed on FIG. 3. A/B EBV type specificity and HLA restriction was determined using standard protocols and demonstrated that the epitope was restricted through HLA B35 and was type A specific (Khanna et al, 1992).

As already mentioned the overlapping peptides were based on the EBV sequence of the B95.8 virus. It was important to determine if field isolates of the virus from different geographical locations also included this sequence. Using PCR sequencing of the EBV sequence present in spontaneous cell lines derived from healthy individuals from Australia (Brisbane), from Papua New Guinea (Goroka and Madang) and from Kenya identified two variants. Two variants of the B95.8 sequence were defined, TVLLHEESM SEQ ID NO:19 and TALLHEESM SEQ ID NO:16 (Table 2).

EXAMPLE 11

Subunit Vaccines 11.1 Vaccine Formulation

Development of new vaccines against a variety of diseases, particularly viral infections, where CD8+ cytotoxic T-cells (CTL) play an important protective role has been hampered by the inability of conventional vaccine formulations to induce protective CTL. Although CTL are readily induced when attenuated viruses are used, in many cases attenuation is difficult, inappropriate and/or unreliable. Conventional killed virus or recombinant protein formulations do not normally gain access to the cytoplasm of antigen presenting cells (APC) and are thus not appropriately processed and presented on class I MHC. A variety of vaccination strategies have been developed to deliver antigen to the cytoplasm of APCs (ie. immunostimulatory complexes [ISCOMs], DNA, fusiogenic proteolysosomes and virus like particles). Such approaches often involve complex formulations which can be difficult to standardise, can result in unstable products and/or may only work for antigens with specific characteristics. An alternative strategy has been to use synthetic peptide CD8+ CTL epitopes as immunogens. This approach has several general advantages; peptides are stable, well defined, easy to manufacture, no infectious material is required for manufacture and the use of potentially pathogenic recombinant proteins can be avoided.

CTL epitopes-formulated with Incomplete Freunds adjuvant (IFA) usually in the presence of a CD4+ helper epitope, have been used to induce CTL in a number of animal systems. Unfortunately, IFA is extremely unlikely, due to its toxicity, to ever be licensed for use in humans. Scalzo, T. et. al. (in preparation) have examined several adjuvants currently approved, or close to approval, for use in humans to ascertain which would be able to induce protective CTL with a synthetic peptide immunogen. Protection was assessed using the Balb/c murine cytomegalovirus (MCMV) model, in which the predominant protective response has been shown to be due to CD8+ CTL directed against the epitope YPHFMPTNL SEQ ID NO:27, derived from the immediate early antigen 1 (IE-1). The presence of active CTL was confirmed using in vitro CTL assays. Scalzo, T. et. al. found that only one formulation, Montanide ISA 720/tetanus toxoid/peptide efficiently induced protective CTL.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 1

CTL peptide epitopes of Epstein-Barr virus within the latent antigens of the virus

| CTL EPITOPE SEQUENCE | EPITOPE INCLUDED IN: | HLA RE-STRICTION | A/B SPECI-FICITY |
|---|---|---|---|
| QAKWRLQTL SEQ ID NO:11 | EBNA3 | B8 | A |
| RYSIFFDY SEQ ID NO:13 | EBNA3 | A24 | A |
| HLAAQGMAY SEQ ID NO:5 | EBNA3 | UNDEFINED | A |
| YPLHEQHGM SEQ ID NO:23 *YPLHKQHGM SEQ ID NO:25 *YRLHEQHGM SEQ ID NO:26 *YPLHEQRGM SEQ ID NO:24 | EBNA3 | B35.(3) | A |
| SVRDRLARL SEQ ID NO:15 | EBNAS | A2 | A/B |
| AVLLHEESM SEQ ID NO:1 #TVLLHEESM SEQ ID NO:19 | EBNA4 | B35 | A |

TABLE 1-continued

CTL peptide epitopes of Epstein-Barr virus within the latent antigens of the virus

| CTL EPITOPE SEQUENCE | EPITOPE INCLUDED IN: | HLA RE-STRICTION | A/B SPECI-FICITY |
|---|---|---|---|
| #TALLHEESM SEQ ID NO:16 VSFIEFVGW SEQ ID NO:22 | EBNA4 | B57 | A/B |
| FRKAQIQGL SEQ ID NO:3 | EBNA6 | B57 | A |
| PYLFWLAAI SEQ ID NO:10 | LMP2A | A23 | A/B |
| TVFYNIPPMPL SEQ ID NO:18 | EBNA2 | HLA DR/DQ | A |
| VIETPYKPTW SEQ ID NO:22 | EBNA4 | B44 | A |
| PGDQLPGFSDGRACPV SEQ ID NO:9 | EBNA3 | A29 | A |

*sequence variants of YPLHEQHGM SEQ ID NO:23
sequence variants of AVLLHEESM SEQ ID NO:1

Existence and Use of Variant Sequences: The epitopes presented in table 1 are based on B95.8 sequence of Epstein-Barr virus. We have examined field isolates of the virus from Papua New Guinea, Australia and Kenya and sequenced these at the sites of two CTL epitopes. These epitopes are AVLLHEESM SEQ ID NO:1 and YPLHEQHGM SEQ ID NO:23. The results presented in Tables 1 and 2 and demonstrate that there is variation at the site of these epitopes in field isolates. At this stage, it is not known whether these variant sequences are CTL epitopes. If subsequent tests demonstrate that these represent active epitopes, then each could be included in a peptide-based vaccine.

TABLE 2

Variation in the HLA B35-restricted EBNA4 Epitope AVLLHEESM in Different Ethnic Groups.

| Virus Isolate | Origin | Epitope Sequence | | | | | | | | | |
|---|---|---|---|---|---|---|---|---|---|---|---|
| B95.8 | Caucasian | GCA | GTT | CTA | CTT | CAC | GAA | GAA | TCC | ATG | SEQ ID NO:29 |
| JB | Caucasian | A | V | L | L | H | E | E | S | M | SEQ ID NO:1 |
| LC | Caucasian | | | | | | | | | | |
| DD | Caucasian | | | | | | | | | | |
| MB | Caucasian | | | | | | | | | | |
| GK | Caucasian | | | | | | | | | | |
| AF6 | Kenyan | | | | | | | | | | |
| AF7 | Kenyan | | | | | | | | | | |
| AF19 | Kenyan | | | | | | | | | | |
| RM | Caucasian | | | | | | | | | | |
| AF1 | Kenyan | | | | | | | | | | |
| LP | Caucasian | | | | | | | | | | |
| AF3 | Kenyan | | | | | | | | | | |
| AF5 | Kenyan | | | | | | | | | | |
| AF13 | Kenyan | | | | | | | | | | |
| JD | Caucasian | ACA | GTT | CTA | CTT | CAC | GAA | GAA | TCC | ATG | SEQ ID NO:30 |
| RE | Caucasian | T | V | L | L | H | E | E | S | M | SEQ ID NO:19 |
| PM | Caucasian | | | | | | | | | | |
| H25 | PNG* High | | | | | | | | | | |
| H19 | PNG High | | | | | | | | | | |
| H33 | PNG High | | | | | | | | | | |
| L5 | PNG Low | | | | | | | | | | |
| L23 | PNG Low | | | | | | | | | | |
| H36 | PNG High | | | | | | | | | | |
| H21 | PNG High | | | | | | | | | | |
| AF16 | Kenyan | | | | | | | | | | |
| H7 | PNG High | | | | | | | | | | |

TABLE 2-continued

Variation in the HLA B35-reatricted EBNA4
Epitope AVLLHEESM in Different Ethnic Groups.

| Virus Isolate | Origin | Epitope Sequence | | | | | | | | | |
|---|---|---|---|---|---|---|---|---|---|---|---|
| L42 | PNG Low | ACA | GCT | CTA | CTT | CAT | GAA | GAA | TCC | ATG | SEQ ID NO:31 |
| H23 | PNG High | T | A | L | L | H | E | E | S | M | SEQ ID NO:16 |
| L43 | PNG Low | | | | | | | | | | |
| H26 | PNG High | | | | | | | | | | |
| L8 | PNG Low | | | | | | | | | | |
| H35 | PNG High | | | | | | | | | | |

*Papua New Guinea

REFERENCES

Khanna, R., Burrows, S., Kurilla, M., Jacob, C. A., Misko, I., Sculley, T. B., Kieff, E., and Moss, D. J. (1992). Localisation of Epstein-Barr virus CTL epitopes in healthy immune donors using recombinant vaccinia: implications for vaccine development. *J. Exp. Med.*, 176, 169–176.

Moss, D. J. and Suhrbier; A. Epstein-Barr virus vaccines: Prospects and limitations, 1993, *Todays Life Sciences* 5, 30–34.

Baer, R., A. T. Bankier, M. D. Biggin, P. L. Desinger, P. J. Farrell, T. J. Gibson, G. Halfull, G. Hudson, C. Satchwell, C. Sequin, P. Fuffnell, and B. Barrell. 1984. DNA sequence and expression of the B95-8 Epstein-Barr virus genome, *Nature* 310, 207–211.

---

We claim:

1. A cytotoxic Epstein-barr virus T-cell epitope, the epitope being selected from the group consisting of QAKWRLQTL (SEQ ID NO:11), RYSIFFDY (SEQ ID NO:13), HLAAQGMAY (SEQ ID NO:5), YPLHEQHGM (SEQ ID NO:23), YPLHKQHGM (SEQ ID NO:25), YRLHEQHGM (SEQ ID NO:26), YPLHEQRGM (SEQ ID NO:24), SVRDRLARL (SEQ ID NO: 15), AVLLHEESM (SEQ ID NO: 1), TVLLHEESM (SEQ ID NO: 19), TALLHEESM (SEQ ID NO: 16), VSFIEFVGW (SEQ ID NO: 22), FRKAQIQGL (SEQ ID NO: 3), PYLFWLAAI (SEQ ID NO: 10), TVFYNIPPMPL (SEQ ID NO: 18), PGDQLPGFSDGRACPV (SEQ ID NO: 9) and VEITPYKPTW (SEQ ID NO: 20).

2. A cytotoxic Epstein-barr virus T-cell epitope, as claimed in claim 1 in which the epitope is QAKWRLQTL (SEQ ID NO:11).

3. A cytotoxic Epstein-barr virus T-cell epitope, as claimed in claim 1 in which the epitope is RYSIFFDY (SEQ ID NO: 13).

4. A cytotoxic Epstein-barr virus T-cell epitope, as claimed in claim 1 in which the epitope is HLAAQGMAY (SEQ ID NO:5).

5. A cytotoxic Epstein-barr virus T-cell epitope, as claimed in claim 1 in which the epitope is YPLHEQHGM (SEQ ID NO:23).

6. A cytotoxic Epstein-barr virus T-cell epitope, as claimed in claim 1 in which the epitope is SVRDRLARL (SEQ ID NO: 15).

7. A cytotoxic Epstein-barr virus T-cell epitope, as claimed in claim 1 in which the epitope is AVLLHEESM (SEQ ID NO: 1).

8. A cytotoxic Epstein-barr virus T-cell epitope, as claimed in claim 1 in which the epitope is VSFIEFVGW (SEQ ID NO: 22).

9. A cytotoxic Epstein-barr virus T-cell epitope, as claimed in claim 1 in which the epitope is FRKAQIQGL (SEQ ID NO: 3).

10. A cytotoxic Epstein-barr virus T-cell epitope, as claimed in claim 1 in which the epitope is PYLFWLAAI (SEQ ID NO: 10).

11. A cytotoxic Epstein-barr virus T-cell epitope, as claimed in claim 1 in which the epitope is TVFYNIPPMPL (SEQ ID NO: 18).

12. A cytotoxic Epstein-barr virus T-cell epitope, as claimed in claim 1 in which the epitope is PGDQLPGFSDGRACPV (SEQ ID NO: 9).

13. A cytotoxic Epstein-barr virus T-cell epitope, as claimed in claim 1 in which the epitope is VEITPYKPTW (SEO ID NO: 20).

14. A cytotoxic Epstein-Barr virus T-cell epitope, as claimed in claim 1 in which the epitope is a variant of YPLHEQHGM (SEQ ID NO:23) the variant being selected from the group consisting of YPLHKQHGM (SEQ ID NO:25), YRLHEQHGM (SEQ ID NO:26) and YPLHEQRGM (SEQ ID NO:24).

15. A cytotoxic Epstein-Barr virus T-cell epitope, as claimed in claim 1 in which the epitope is a variant of AVLLHEESM (SEQ ID NO: 1), the variant being selected from the group consisting of TVLLHEESM (SEQ ID NO: 19) and TALLHEESM (SEQ ID NO: 16).

16. A method of preparing a composition, method comprising admixing at least one cytotoxic Epstein-Barr virus T-cell epitope as claimed in any one of claims 1–15 with at least one pharmaceutically acceptable adjuvant, carrier, diluent or excipient.

* * * * *

UNITED STATES PATENT AND TRADEMARK OFFICE
CERTIFICATE OF CORRECTION

PATENT : 5,869,453
DATED : February 9, 1999
INVENTOR(S) : Denis James Moss, et al.

It is certified that error appears in the above-identified patent and that said Letters Patent is hereby corrected as shown below:

On the title page:
    Item [75], line 3, delete "Hentson", and insert --Herston--; and
    Item [73], line 3, after "Queensland", delete ", Australia", and insert the following:
        --; COMMONWEALTH SCIENTIFIC AND INDUSTRIAL RESEARCH
            ORGANISATION, Australian Capital Territory;

THE UNIVERSITY OF MELBOURNE, Victoria;

THE WALTER AND ELIZA HALL INSTITUTE OF MEDICAL RESEARCH, Victoria;

BIOTECH AUSTRALIA PTY LIMITED, New South Wales; and

CSL LIMITED, Victoria, all of Australia --.

UNITED STATES PATENT AND TRADEMARK OFFICE
CERTIFICATE OF CORRECTION

PATENT : 5,869,453

DATED : February 9, 1999

INVENTOR(S) : Denis James Moss, et al.

It is certified that error appears in the above-identified patent and that said Letters Patent is hereby corrected as shown below:

In claim 16, column 24, line 9, after "composition,", insert -- the --.

Signed and Sealed this

Twenty-second Day of June, 1999

*Attest:*

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT : 5,869,453
DATED : February 9, 1999
INVENTOR(S) : Denis James Moss, et al.

It is certified that error appears in the above-identified patent and that said Letters Patent is hereby corrected as shown below:

On the title page:
    Item [75], line 3, delete "Hentson", and insert --Herston--; and
    Item [73], line 3, after "Queensland", delete ", Australia", and insert the following:

--; COMMONWEALTH SCIENTIFIC AND INDUSTRIAL RESEARCH ORGANISATION, Australian Capital Territory;

THE UNIVERSITY OF MELBOURNE, Victoria;

THE WALTER AND ELIZA HALL INSTITUTE OF MEDICAL RESEARCH, Victoria;

BIOTECH AUSTRALIA PTY LIMITED, New South Wales; and

CSL LIMITED, Victoria, all of Australia --.

UNITED STATES PATENT AND TRADEMARK OFFICE
CERTIFICATE OF CORRECTION

PATENT : 5,869,453
DATED : February 9, 1999
INVENTOR(S) : Denis James Moss, et al.

It is certified that error appears in the above-identified patent and that said Letters Patent is hereby corrected as shown below:

In claim 16, column 24, line 9, after "composition,", insert -- the --.

Signed and Sealed this

Thirty-first Day of August, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:1:

Ala  Val  Leu  Leu  His  Glu  Glu  Ser  Met
    1                          5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

Glu  Glu  Ser  Met  Gln  Gly  Val  Gln  Val
    1                          5

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

Phe  Arg  Lys  Ala  Gln  Ile  Gln  Gly  Leu
    1                          5

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:4:

His  Glu  Glu  Ser  Met  Gln  Gly  Val  Gln
    1                            5

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:5:

His  Leu  Ala  Ala  Gln  Gly  Met  Ala  Tyr
    1                            5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:6:

Leu  His  Glu  Glu  Ser  Met  Gln  Gly  Val
    1                            5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:7:

Leu  Leu  His  Glu  Glu  Ser  Met  Gln  Gly
    1                            5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:8:

Met  Gln  Gly  Val  Gln  Val  His  Gly  Ser
    1                            5

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( x i ) SEQUENCE DESCRIPTION: SEQ ID NO:9:

```
Pro Gly Asp Gln Leu Pro Gly Phe Ser Asp Gly Arg Ala Cys Pro Val
1               5                   10                  15
```

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:10:

```
Pro Tyr Leu Phe Trp Leu Ala Ala Ile
1               5
```

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:11:

```
Gln Ala Lys Trp Arg Leu Gln Thr Leu
1               5
```

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:12:

```
Gln Gly Val Gln Val His Gly Ser Met
1               5
```

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS:
        (D) TOPOLOGY: linear (xi) SEQUENCE DESCRIPTION: SEQ ID NO:13:

```
Arg Tyr Ser Ile Phe Phe Asp Tyr
1               5
```

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:14:

```
Ser Met Gln Gly Val Gln Val His Gly
1               5
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS:

(D) TOPOLOGY: linear (xi) SEQUENCE DESCRIPTION: SEQ ID NO:15:

Ser Val Arg Asp Arg Leu Ala Arg Leu
1               5

(2) INFORMATION FOR SEQ ID NO:16:

(i) SEQUENCE CHARACTERISTICS:
    (A) LENGTH: 9 amino acids
    (B) TYPE: amino acid
    (C) STRANDEDNESS:
    (D) TOPOLOGY: linear (xi) SEQUENCE DESCRIPTION: SEQ ID NO:16:

Thr Ala Leu Leu His Glu Glu Ser Met
1               5

(2) INFORMATION FOR SEQ ID NO:17:

(i) SEQUENCE CHARACTERISTICS:
    (A) LENGTH: 9 amino acids
    (B) TYPE: amino acid
    (C) STRANDEDNESS:
    (D) TOPOLOGY: linear (xi) SEQUENCE DESCRIPTION: SEQ ID NO:17:

Thr Ala Val Leu Leu His Glu Glu Ser
1               5

(2) INFORMATION FOR SEQ ID NO:18:

(i) SEQUENCE CHARACTERISTICS:
    (A) LENGTH: 11 amino acids
    (B) TYPE: amino acid
    (C) STRANDEDNESS:
    (D) TOPOLOGY: linear (xi) SEQUENCE DESCRIPTION: SEQ ID NO:18:

Thr Val Phe Tyr Asn Ile Pro Pro Met Pro Leu
1               5                   10

(2) INFORMATION FOR SEQ ID NO:19:

(i) SEQUENCE CHARACTERISTICS:
    (A) LENGTH: 9 amino acids
    (B) TYPE: amino acid
    (C) STRANDEDNESS:
    (D) TOPOLOGY: linear (xi) SEQUENCE DESCRIPTION: SEQ ID NO:19:

Thr Val Leu Leu His Glu Glu Ser Met
1               5

(2) INFORMATION FOR SEQ ID NO:20:

(i) SEQUENCE CHARACTERISTICS:
    (A) LENGTH: 10 amino acids
    (B) TYPE: amino acid
    (C) STRANDEDNESS:
    (D) TOPOLOGY: linear (xi) SEQUENCE DESCRIPTION: SEQ ID NO:20:

Val Glu Ile Thr Pro Tyr Lys Pro Thr Trp
1               5                   10

(2) INFORMATION FOR SEQ ID NO:21:

( i ) SEQUENCE CHARACTERISTICS:
   ( A ) LENGTH: 9 amino acids
   ( B ) TYPE: amino acid
   ( C ) STRANDEDNESS:
   ( D ) TOPOLOGY: linear ( x i ) SEQUENCE DESCRIPTION: SEQ ID NO:21:

```
Val  Leu  Leu  His  Glu  Glu  Ser  Met  Gln
1                   5
```

( 2 ) INFORMATION FOR SEQ ID NO:22:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( x i ) SEQUENCE DESCRIPTION: SEQ ID NO:22:

```
Val  Ser  Phe  Ile  Glu  Phe  Val  Gly  Trp
1                   5
```

( 2 ) INFORMATION FOR SEQ ID NO:23:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( x i ) SEQUENCE DESCRIPTION: SEQ ID NO:23:

```
Tyr  Pro  Leu  His  Glu  Gln  His  Gly  Met
1                   5
```

( 2 ) INFORMATION FOR SEQ ID NO:24:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( x i ) SEQUENCE DESCRIPTION: SEQ ID NO:24:

```
Tyr  Pro  Leu  His  Glu  Gln  Arg  Gly  Met
1                   5
```

( 2 ) INFORMATION FOR SEQ ID NO:25:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( x i ) SEQUENCE DESCRIPTION: SEQ ID NO:25:

```
Tyr  Pro  Leu  His  Lys  Gln  His  Gly  Met
1                   5
```

( 2 ) INFORMATION FOR SEQ ID NO:26:

( i ) SEQUENCE CHARACTERISTICS:
      ( A ) LENGTH: 9 amino acids
      ( B ) TYPE: amino acid
      ( C ) STRANDEDNESS:
      ( D ) TOPOLOGY: linear ( x i ) SEQUENCE DESCRIPTION: SEQ ID NO:26:

```
Tyr  Arg  Leu  His  Glu  Gln  His  Gly  Met
1                   5
```

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( x i ) SEQUENCE DESCRIPTION: SEQ ID NO:27:

```
Tyr  Pro  His  Phe  Met  Pro  Thr  Asn  Leu
1                   5
```

( 2 ) INFORMATION FOR SEQ ID NO:28:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( x i ) SEQUENCE DESCRIPTION: SEQ ID NO:28:

```
Val  Thr  Ala  Val  Leu  Leu  His  Glu  Glu  Ser  Met  Gln  Val  Gln  Val  His
1                   5                             10                            15
Gly  Ser  Met
```

( 2 ) INFORMATION FOR SEQ ID NO:29:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
GCAGTTCTAC  TTCACGAAGA  ATCCATG                                              27
```

( 2 ) INFORMATION FOR SEQ ID NO:30:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
ACAGTTCTAC  TTCACGAAGA  ATCCATG                                              27
```

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
ACAGCTCTAC  TTCATGAAGA  ATCCATG                                              27
```

( 2 ) INFORMATION FOR SEQ ID NO:32:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:33:

GACGAGACAG CTACCAG    17

(2) INFORMATION FOR SEQ ID NO:34:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:34:

GAGATACAGG GGGCAAG    17

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:35:

TTGTTGAGGA TGACGACG    18

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:35:

CAGTAGGGTT GCCATAAC    18

(2) INFORMATION FOR SEQ ID NO:36:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:36:

Tyr Leu Pro His Glu Gln His Gly Met
1               5